United States Patent [19]

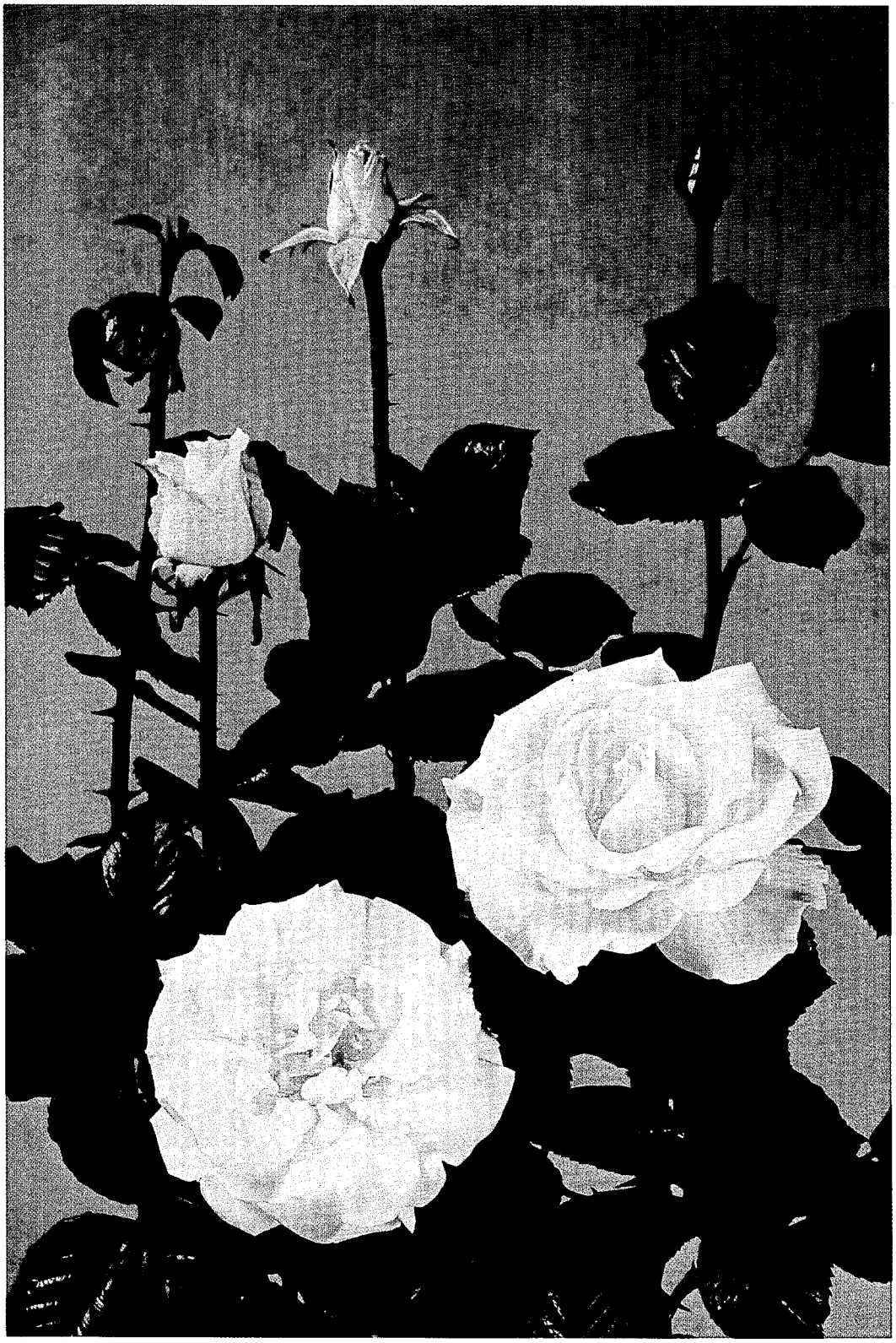

McGredy, IV

[11] Plant 4,063

[45] June 21, 1977

[54] ROSE PLANT

[75] Inventor: Samuel McGredy, IV, Auckland, New Zealand

[73] Assignee: Armstrong Nurseries, Inc., Ontario, Calif.

[21] Appl. No.: 680,507

[22] Filed: Apr. 26, 1976

[51] Int. Cl.[2] ..... A01H 5/00

[52] U.S. Cl. ..... Plt./15

[58] Field of Search ..... Plt./15

*Primary Examiner*—Robert E. Bagwill

*Attorney, Agent, or Firm*—Synnestvedt and Lechner

[57] ABSTRACT

A tall outdoor bush rose plant of the Grandiflora class, having a vigorous much-branched habit of growth and carrying strong, short to medium length flowering stems, sometimes with one bloom or sometimes with three or more blooms to the stem. Resistance to mildew is significantly better than with plants of the same genus under comparable conditions. The general color effect is between brilliant yellow and moderate orange yellow when the flower is freshly opened. This lightens to generally lighter tones of the same shading after the flower has been open for several days. Blooms have a slight pollen fragrance.

1 Drawing Figure

1

This invention relates to a new Grandiflora rose. The plant is of the tall bushy outdoor type, cultivated primarily for garden decoration. It was first propagated by Samuel McGredy, IV, in Portadown, Northern Ireland, and was propagated in Ontario, Calif., from the budwood of that first propagation. The plant described herein is the plant asexually reproduced in California, and any comparison to other varieties of Grandiflora rose is based upon plants grown in Ontario, Calif., under comparable conditions. It blooms abundantly outdoors, and almost continually during the growing season.

The seed parent was the variety known as "Peer Gynt", and the pollen parent was "Kiskadee". The plant holds its distinguishing characteristics through succeeding propagations by budding.

The new variety bears its flowers sometimes singly on strong medium to long stems, sometimes three or more to a stem. The stems are strong, and of short to medium length. The fragrance is slight and pollen-like.

This new cultivar differs most significantly from its seed parent, Peer Gynt, in the following ways:

Peer Gynt is classed as a Hybrid Tea while the new rose is classed as a Grandiflora.

Peer Gynt has large flowers containing 50 petals, while this new cultivar has average size flowers with 20 to 25 petals plus 15 to 30 petaloids.

Peer Gynt is a weak-growing plant, in Southern California, whereas this new rose is very vigorous in growth in that area.

The new cultivar differs most notably from its pollen parent, Kiskadee, in the following ways:

Kiskadee is classed as a Floribunda, while the new rose is classed as a Grandiflora.

Although petal count averages 25 in Kiskadee, and ranges from 20 to 25 in the new cultivar, the new rose has 15 to 30 petaloids in addition to its petals, and Kiskadee has few, if any.

Open flower color in Kiskadee shows very little fading from its original bright yellow as the flower ages, while the new cultivar becomes a noticeably lighter shade of yellow with age.

The plant of the new cultivar is taller-growing than the plant of its pollen parent, Kiskadee.

The accompanying drawing illustrates the plant in color and shows the flowering thereof from bud to full bloom.

2

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average length to long and average caliper, being erect with numerous small prickles and some stipitate glands. The color is between Moderate Yellow Green, 5GY5/6, and Strong Yellow Green, 2.5GY6/8.

Before the calyx breaks, the bud is small in size, medium length, is pointed and ovoid, with a conspicuous neck. The surface of the bud has foliaceous appendages and stipitate glands, with slender foliaceous parts usually extending beyond the tip of the bud equal to one-half or more of its length.

As the calyx breaks, the color is near Vivid Greenish Yellow, 7.5Y8/12.

The inner surface of the sepals carries a fine, wooly tomentum and margins with stipitate glands, except where margins were covered by other sepals before the buds opened. The outside surface of the sepals carries stipitate glands.

As the first petal opens, it is average in size, of medium length, and ovoid to urn-shaped. The color on the outside of the petal is between Vivid Yellow, 5Y8/12, and Strong Orange Yellow, 10YR7/10, sometimes lightly blushed with near Strong Red, 5R4/12, near the margins. The inner surface shows the same coloration as the outer surface.

The bud opens up well, and is not retarded or prevented from opening by cold, hot, wet, or dry weather.

BLOOM

The size of the bloom when fully open is average, being from 8 to 11 centimeters in diameter. The petalage is double, with from 20 to 25 petals arranged regularly, plus 15 to 30 petaloids. The bloom is high centered at first, becoming open to cupped.

The petals remain at first somewhat tightly cupped, with tips refluxed outward. Later, at maturity, the petals become loosely cupped, with tips reflexed outward.

The petals are of medium thickness, the inside being slightly shiny to velvety while the outside is slightly shiny to satiny. The outside petals are nearly round, the intermediate petals broadly obovate. Inside petals are broadly obovate to irregular. The colors may be modified by being bordered or margined, or shaded and/or washed or tinted with other colors.

The paragraphs immediately following describe color values observed in a flower newly opened in the month of October. The plant had been grown outdoors, in Ontario, Calif.

The outer surface of the outside petal is between Brilliant Yellow, 5Y9/9, and Moderate Orange Yellow, 10YR8/10, sometimes with a light blush of near Moderate Red, 2.5R4/10, near the margins. The inner surface of the outside petal varies between Brilliant Yellow, 5Y9/9, and Moderate Orange Yellow, 10YR8/10, sometimes also with a light blush of near Moderate Red, 2.5R4/10, near the margins.

The coloration of the outer and inner surfaces of the intermediate and the inner petals is very similar to that of the outer petals, ranging from a pale yellow to the deeper shades noted. The unavoidable highlights incident to photography do not do justice to the fact that the petal coloration is unusually close to being uniform, varying primarily in degree only, between the generally yellow color of the bloom The paragraphs immediately following describe the color values observed in a bloom which had been open for 3 days, outdoors, in the month of October. The plant had been grown outdoors, in Ontario, Calif.

The outer surface of the outside petal ranged from a very light yellow to a color near Moderate Orange Yellow, 10YR8/10, sometimes with a light blush near Deep Pink, 10RP6/12, near the margins. The same color values characterized the inner surface of the outside petal.

The outer surface and the inner surface of the inside petal held the same color values as found on the outside petal.

The general color effect of the newly opened flower is between Brilliant Yellow, 5Y9/9, and Moderate Orange Yellow, 10YR8/10. After being three days open, the bloom is a light yellow. The petals drop off cleanly, except for the petaloids, and are not particularly affected by cold, hot, wet, or dry weather.

The flower on the bush in the garden persists for from 3 to 5 days in the month of October, in the locality named. Cut roses grown outdoors and kept at living-room temperatures will last from 3 to 4 days in the month of October.

REPRODUCTIVE ORGANS

Stamens: The stamens are average in number, regularly arranged about the pistils, a few of them being mixed with petaloids, and a few tucked in the calyx.

Filaments: The filaments are medium length and between Vivid Yellow, 5Y8/12, and Strong Reddish Orange, 7.5R5/13. Most are with anthers.

Anthers: The anthers are of medium size, all opening approximately at once. Just before pollen is released, the color along the margins is between Light Orange, 5YR8/7, and Strong Orange, 5YR7/11. On both the upper and lower sides of the interior surfaces, the color is near Brilliant Yellow, 5Y9/9.

Pollen: There is a moderate amount of pollen, which is Moderate Orange Yellow, 10YR8/10, in color.

Pistils: The pistils are approximately 65 in number, this being average.

Styles: The styles are moderately even, average length and caliper, bunched and hairy. The color varies from Brilliant Greenish Yellow, 10Y9/9, near the base, to near Vivid Red, 5R5/13, just below the stigma.

Stigma: The stigma is near Moderate Orange Yellow, 10YR8/10, in color.

Ovaries: Most of the ovaries are enclosed in the calyx.

Hips: The hips are short to average in length and globular. At one-half maturity, they are near Brilliant Yellow Green, 5GY8/8, in color, smooth, with fleshy walls.

Seeds: The new variety produced few seeds, from 5 to 10 in number, and these were from small to medium in size.

FOLIAGE

The compound leaves usually comprise three to seven leaflets. They are abundant, from medium size to large, moderately heavy to somewhat leathery and glossy in texture. The leaflets are ovate, with apex acute, base obtuse, and margin usually simple serrate.

The mature foliage displays upon its upper surface a coloration which is between Moderate Olive Green, 7.5GY4/4, and Dark Grayish Green, 10GY3/2. The under surface is near Brilliant Yellow Green, 7.5GY8/7, overlaid with gray.

The young foliage on its upper surface is near Strong Yellow Green, 2.5GY6/8, in color, strongly overlaid with near Moderate Reddish Brown, 7.5R3/6. On its under surface it is near Dark Red, 5R3/7.

The rachis is average in size, grooved, with some stipitate glands on the edges. The under side is sparsely prickly, with a few stipitate glands.

The stipules are medium in both length and width, with medium-length points turning out at an angle of less than 90°, slightly recurved toward the stem.

The plant is almost resistant to mildew, when compared with other varieties now in commerce under comparable conditions, when grown at Ontario, Calif.

GROWTH

The plant is tall, upright, bushy, and much branched. It displays a very vigorous growth. The canes are medium to heavy in caliper.

The main stems are between Light Olive, 5Y5/6, and Moderate Olive, 5Y4/3, in color. They carry several large prickles which are medium-length to long, almost straight, with medium-length moderately broad bases. The coloration of these large prickles is between gray and Strong Yellowish Brown, 10YR5/6. There are few small prickles, and their color is the same as that of the large prickles. There are no hairs.

The branches are a color between Light Olive, 10Y5/5, and Moderate Olive, 10Y4/3. There are several large prickles, medium-length to long, almost straight, with medium-length moderately broad bases. The coloration of these large prickles is between Strong Yellow Brown, 7.5YR5/7, and Moderate Brown, 7.5YR4/5. There are few small prickles, and their color is the same as that of the large prickles. There are no hairs.

New shoots have a color between Strong Yellow Green, 5GY6/8, and Moderate Yellow Green, 5GY5/6, lightly to moderately overlaid with Dark Red, 5R3/7. There are from few to several large prickles, which are long, almost straight to hooked slightly upward, with medium-length, moderately broad bases. These prickles are the same color as the new shoots. There are from none to few small prickles, and their coloration is the same as that of the large prickles. There are no hairs.

I claim:

1. The new and distinct variety of Grandiflora rose plant substantially as herein illustrated and described, which is characterized by a plurality of the following features, in combination, namely a notably vigorous, upright habit of growth, many-branched and tall, with abundant glossy medium-sized foliage, said plant being more hardy and more resistant to mildew than is usual with plants of the same species grown under comparable conditions; a nearly continuous blooming habit throughout the season; blooms with double petalage which have a predominantly yellow color effect, varying mainly in depth of shade, and having a mild, pollen-like fragrance; many of the flowering stems carrying only a single flower.

* * * * *

UNITED STATES PATENT AND TRADEMARK OFFICE

CERTIFICATE OF CORRECTION

PATENT NO. : PP-4063

DATED : June 21, 1977

INVENTOR(S) : Samuel McGredy, IV

It is certified that error appears in the above-identified patent and that said Letters Patent are hereby corrected as shown below:

Column 2, line 45 - "refluxed" should be --reflexed--.

Column 3, line 26 - following "bloom" insert

--and the deeper shades described.--

Signed and Sealed this

*Sixth* Day of *September 1977*

[SEAL]

*Attest:*

RUTH C. MASON
*Attesting Officer*

LUTRELLE F. PARKER
*Acting Commissioner of Patents and Trademarks*